United States Patent [19]

Hager, Jörg et al.

[11] Patent Number: 4,874,553
[45] Date of Patent: Oct. 17, 1989

[54] AQUEOUS PHOSPHOLIPID SOLUTIONS CONTAINING A SOLUBILIZING AGENT

[75] Inventors: Hager, Jörg; Miklos Ghyczy, both of Cologne; Vincent Feyen, Bergheim; Paul Imberge, Pulheim-Sinthern; Ulrich Brandenburg, Cologne; Peter Wilperath, Bergisch Gladbach, all of Fed. Rep. of Germany

[73] Assignee: A. Nattermann & Cie. GmbH, Cologne, Fed. Rep. of Germany

[21] Appl. No.: 24,565

[22] Filed: Mar. 11, 1987

[30] Foreign Application Priority Data

Mar. 14, 1986 [DE] Fed. Rep. of Germany ....... 3608455

[51] Int. Cl.$^4$ .............................................. C07E 9/10
[52] U.S. Cl. .................................................. 260/403
[58] Field of Search ......................................... 260/403

[56] References Cited

U.S. PATENT DOCUMENTS

| 1,938,864 | 12/1933 | Rewald | 167/16 |
| 2,258,832 | 10/1941 | Weitkamp | 167/28 |
| 3,943,066 | 3/1976 | Fusey | 252/356 |
| 4,174,296 | 11/1979 | Kass | 260/403 |
| 4,339,391 | 7/1982 | Hoffmann et al. | 260/403 |
| 4,482,474 | 11/1984 | Biedermann et al. | 252/311 |

FOREIGN PATENT DOCUMENTS 498895 3/1979 Australia .
1168465 6/1984 Canada .

*Primary Examiner*—Anton H. Sutto
*Attorney, Agent, or Firm*—Burns, Doane, Swecker & Mathis

[57] ABSTRACT

Liquid phospholipid-containing products in an aqueous medium which contains 5–80% by weight of phospholipids and 3–10% by weight of one or more compounds of the general formula $$RO-A-NR_1R_2R_3$$

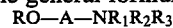

their preparation and their use, for example as additives for improving plant treatment agents.

12 Claims, No Drawings

AQUEOUS PHOSPHOLIPID SOLUTIONS CONTAINING A SOLUBILIZING AGENT

Lecithins and phospholipids play an important role both in the foodstuffs industry and in the chemical and pharmaceutical industry because they have outstanding physiological properties and furthermore many products can be improved physically with their aid. This is to be attributed, inter alia, to emulsifying, softening, colloidal, antioxidative and surface-active effects. The most important lecithin processers are: the oil and margarine industry, the feedstuffs industry, the confectionery industry, the paints industry, the bakery industry, the petroleum industry, the leather industry, the textile industry, the rubber industry, the plant protection agent industry, the pharmaceutical industry, the cosmetics industry and the soap industry. Lecithin has a combined effect in many production processes, which makes is superior to synthetic substances. It is moreover acceptable from the point of view of nutritional physiology and is therefore suitable for use in the foodstuffs industry.

Phospholipids occur widely in nature and can be obtained from animal and vegetable materials. The main sources are eggs (egg lecithin), oil seeds and oil fruits, such as, for example, coconut copra, palm kernels, peanuts, rape, sunflower seeds, soybean, oil palms and olives. Phospholipids are chiefly obtained as a by-product in the production of vegetable oils.

Vegetable oils are obtained either by pressing or by extraction with fat solvents. Both processes are also frequently used, in that pressing is first carried out and the pressed residues thereby obtained are then extracted. The pressed residue or the extraction waste is the most important by-product of oil production in terms of quantity. The pressed residue and the extraction waste is a much sought after concentrated feed for agriculture because of its high protein content.

The fats and oils obtained by pressing or extraction must be subjected to considerable purification if they are used for foodstuffs purposes. This purification is also called refining. One of the most important purification steps is so-called slime removal, in which undesired phospholipids dissolved out of the oil seed together with the neutral oil are removed from the crude oil in order to increase the stability and storability of the oils.

Slime removal is carried out by passing small amounts of steam or water into the crude oil at elevated temperatures. During this procedure, a viscous mass, the so-called lecithin sludge, forms. These lecithin sludges have various compositions, depending on their origin:

14–36% by weight of vegetable oil
27–56% by weight of water
59–8% by weight of phospholipids.

This by-product of oil production is either sprayed directly again from the waste and used as a feedstuff, or is evaporated down to a residual water content of 0.5–2% in an evaporator at elevated temperatures (about 80° C.) for a relatively long time (from 6 to 12 hours) or at 100° C. in a thin film evaporator with shorter residence time. This drying of the lecithin sludge gives the commercially available crude lecithin. The most important crude lecithin is soya lecithin, which after drying contains about 52% by weight of phospholipids
35% by weight of oils and fatty acids
10% by weight of glycolipid and sugars
2% by weight of non-hydrolizable constituents
and 1% by weight of water So-called de-oiled phospholipids (or de-oiled crude lecithin, which contains only small amounts of oil and other concomitant lipids) are obtained by treatment with corresponding solvents, for example with acetone.

The lecithin fractions obtained have varying phospholipid compositions, depending on their origin: soya lecithin: about 30% of phosphatidylcholine, 1–2% of lysophosphatidylcholine, 22% of phosphatidylethanolamine, 1–2% of lysophosphatidylethanolamine, 3–4% of phosphatidylserine, 18% of phosphatidylinositol, 13% of phytoglycolipids, 2% of phosphatidic acid and 8% of concomitant lipids.

Egg lecithin: 73% of phosphatidylcholine, 5–6% of lysophosphatidylcholine, 15% of phosphatidylethanolamine, 2–3% of lysophosphatidylethanolamine, 1% of phosphatidylinositol, 2–3% of sphingomyelin and 1% of plasmalogen.

Rape lecithin: 30–32% of phosphatidylcholine, 3% of lysophosphatidylcholine, 30–32% of phosphatidylcholine, 3% of lysophosphatidiylethanolamine, 14–18% of phosphatidylinositol, 1% of lysophosphatidylinositol, 10% of phytoglycolipids, 1% of phosphatidic acid and 2–3% of concomitant lipids.

Safflower lecithin: 32–39% of phosphatidylcholine, 1–2% of lysophosphatidylcholine, 14–17% of phosphatidylethanolamine, 2% of lysophosphatidylethanolamine, 21–27% of phosphatidylinositol, 1% of lysophosphatidylinositol and 15–28% of concomitant lipids.

The individual lecithins can also be purified by known processes and the corresponding phospholipids can be separated into the individual constituents, such as phosphatidylcholine, phosphatidylethanolamine, phosphatidylinositol, phosphatidylserine, phosphatidylglycerol, lysophosphatidylcholine, lysophosphatidylethanolamine, lysophosphatidylserine and lysophosphatidylglycerol, or olefinic mixtures can also be prepared.

Thus, for example, pure phospholipid products which can have, for example, the following composition (European Patent 68,295) are commercially available.

Phospholipon ® 25: 25% of phosphatidylcholine, 25% of phosphatidylethanolamine, 20% of phosphatidylinositol Phospholipon ® 55: 55% of phosphatidylcholine, 25% of phosphatidylethanolamine, 2% of phosphatidylinositol Phospholipon ® 80: 80% of phosphatidylcholine, 10% of phosphatidylethanolamine, Phospholipon ® 100: 96% of phosphatidylcholine Phospholipon ® 100 H: 96% of hydrogenated phosphatidylcholine Phospholipon ® 38: 38% of phosphatidylcholine, 16% of N-actyl-phosphatidylethanolamine, 4% of phosphatidylethanolamine The phospholipid mixtures of widely varying compositions, from lecithin wet sludge, crude lecithin and de-oiled lecithin to phospholipid mixtures of defined composition or even pure phospholipids, such as, for example, phosphatidylcholine, have physical properties which vary widely from one to the other. These phospholipid mixtures have widely varying consistencies from liquid to viscous-plastic.

In order to be able to put these mixtures to use, they must be brought into the appropriate processable form by suitable measures with the addition of, for example, emulsifiers, solvents, liquefiers and the like. For many fields of use, it is desirable to be able to dissolve or emulsify the water-insoluble phospholipid mixtures in water. There have already been many attempts to dissolve or emulsify various phospholipid mixtures or phospholipid-containing mixtures in water, and in European Patent 98,561, for example, organic solvents and emulsifiers are added. In German Patent 1,141,639, pure phosphatidylcholine is rendered water-soluble by addition of bile acids. In German Auslegeschrift 1,227,191, lecithins are emulsified with aliphatic polyalcohols in the presence of ethanol in water. In German Offenlegungsschrift 1,617,542, de-oiled crude lecithin is rendered water-soluble in aqueous sugar-containing alcohols. According to U.S. Pat. No. 2,402,690, oil-containing lecithins can be rendered water-dispersible by addition of monoglycerides. In German Patent 3,218,027, liquefaction and water-solubility of phospholipids is obtained by addition of hydroxyethyl-fatty acid amides. All the processes to date have the disadvantage that they have each been developed individually for a particular phospholipid or lecithin mixture and therefore fail when applied to another mixture, for example lecithin wet sludge.

The aim of the present invention was therefore to find an additive and a method with which phospholipid mixtures of the most diverse concentration and composition can be dissolved, emulsified or dispersed in water.

It has now been found, surprisingly, that phospholipid mixtures of the most diverse concentration and composition can be rendered water-dispersible or -soluble by adding 3–10% of one or more compounds of the general formula I $$RO-A-NR_1R_2R_3$$

wherein R denotes hydrogen or an acyl radical of a carboxylic acid with 1–22 carbon atoms, A denotes a straight-chain or branched alkylene group with 1–10 carbon atoms and $R_1$, $R_2$ and $R_3$ can be identical or different and denote hydrogen or an alkyl group with 1–8 carbon atoms, which, if appropriate, can be present as salts. Preferred compounds of the formula I are those in which R denotes a hydrogen atom, A denotes a straight-chain alkylene group with 2 to 4 carbon atoms and $R_1$, $R_2$ and $R_3$ are identical or different and denote hydrogen or methyl. Examples of compounds of the formula I are: dimethylaminomethylacetic acid esters, 2-dimethylaminoethylacetic acid esters, 1-methylamino-2-hydroxy-ethane, 1-dimethylamino-2-hydroxy-ethane, 1-trimethylamino-2-hydroxy-propane, 1-dimethylamino-2-hydroxy-butane, 1-hydroxy-2-trimethylamino-ethane hydrochloride, 1-hydroxy-2-methylamino-hexane, 1-amino-2-hydroxy-ethane, 1-amino-3-hydroxy-propane, trimethylaminoethyllinoleic acid esters, 2-aminoethyllinoleic acid esters, 1-amino-2-hydroxy-propane, 1-dimethylamino-2-hydroxy-propane, 1-trimethylamino-2-hydroxy-propane, 1-amino-3-hydroxy-butane, 1-trimethylamino-3-hydroxy-propane, 4-hydroxy-1-trimethylamino-butane, 1-amino-1-hydroxy-propane and 1-trimethylamino-1-hydroxy-propane hydrochloride.

1-Amino-2-hydroxy-ethane and 1-hydroxy-2-trimethylamino-ethane and salts thereof are particularly preferred and are added individually or in a mixture in concentrations of 3–10% by weight to the phospholipid mixture to be dissolved. If appropriate, the amount of 10% by weight can also be exceeded. Preferably, however, 5–7% by weight of the compound or mixtures thereof are added, and the addition of 6% by weight is particularly preferred. Mixtures of 1-amino-2-hydroxyalkanes and 1-hydroxy-2-trimethylamino-alkanes are particularly advantageous, 0.8–1.2% by weight of the aminohydroxyalkane and 4.8–5.2% by weight of trimethylaminohydroxyalkane being used together. Other customary auxiliaries can also be added if appropriate, such as, for example, preservatives and emulsifiers. Possible preservatives are, for example, formalin solutions, Preventol D 3, benzoic acid or sorbic acid.

Emulsifiers which can be used are, for example, fatty alcohol ethoxylates (for example the commercial products Merlipal, Lorox, Steinapal and Emulgien), ethoxylated fatty amines (for example the commercial products Ethomeen, Genamin and Araphen), alkylphenol ethoxylates (for example the commercial products Antarox and Atlas-Renex products), nonylphenol polyglycol ethers, ethoxylated fatty acid esters, sorbitan fatty acid esters, ethoxylated sorbitan fatty acid esters, betaines, ethoxylated coconut oil amine, alkyl polyglycol ethers, polyoxyethylene (20) sorbitan monolaurate, polyoxyalkylene (20) sorbitan monopalmitate, glycerol polyethyleneglycol oxystearate, caproic acid hydroxyethylamide, alkylphenol polyglycol ethers and polyethylene-castor oil.

All products in which the phospholipid content can vary from 5 to 98%, such as, for example, lecithin wet sludges, which have the following composition, depending on their origin:

14–36% of vegetable oils
27–56% of water
59–8% of phospholipids or highly pure phospholipids with up to 98% of phosphatidylcholine, can be used as the phospholipid-containing mixtures.

In addition to the phospholipids, all the constituents originating from the production of the phospholipids, such as, for example, sterins, oils, sugars, water, glycolipids and the like, can be present in the mixture.

The new phospholipid-products can be used as additives for pesticides and fertilizers, especially for foliage fertilizers and also as additives for food, feeds, cosmetics and as dispersing agents for technical applications. The new phospholipid-product can also be used as carrier medium for biological activ substances like drugs, pesticides, nutrients, fertilizers, vitamins etc.

EXAMPLE 1

43.25% by weight of sunflower lecithin wet sludge with the following composition:
16.21 % by weight of oil
52.2% by weight of water
31.6% by weight of phospholipids are stirred into a solution of 1.0% by weight of 1-amino-2-hydroxy-ethane and 5.0% by weight of 1-hydroxy-2-trimethylamino-ethane hydrochloride as well as 1.0% by weight of Preventol D 3 (preservative: synergistically active mixture of arylmethanol and halogenoalkylacylaminomethanol) and 49.75% by weight of water.

The resulting emulsion with a pH of about 8 and a viscosity of about 100 mPa.s was stored for several months and was technologically stable.

EXAMPLE 2

30% by weight of soya lecithin of the following composition:

36% by weight of soya oil
64% by weight of phospholipids are stirred into a mixture consisting of 1.0% by weight of 1-amino-2-hydroxy-ethane, 1.5% by weight of ethoxylated coconut oil amine (emulsifier), 1.5% by weight of alkylpolyglycol ether (emulsifier), 0.54% by weight of formalin, 5.0% by weight of 1-hydroxy-2-trimethylamino-ethane hydrochloride and 60.46% by weight of water at room temperature.

The resulting formulation with a pH of 9 and a viscosity of less than 100 mPa.s was stored for some months and was technologically stable.

EXAMPLE 3

30% by weight of rape lecithin are stirred into a mixture consisting of 1.0% by weight of aminoalkanol, 1.5% by weight of ethoxylated coconut alkylamine, 1.5% by weight of alkylpolyglycol ether, 5.0% by weight of 1-hydroxy-2-trimethylamino-ethane hydrochloride, 0.54% by weight of formalin solution and 60.46% by weight of water at room temperature.

The resulting formulation with a pH of 8.5 and a viscosity of less than 100 mPa.s was stored for several months and was technologically stable.

EXAMPLE 4

49.8% by weight of sunflower lecithin wet sludge are stirred into a mixture consisting of 1.0% by weight of aminoalkanol, 3.0% by weight of ethoxylated oxo-alcohol, 5.0% by weight of trimethylamino-alkanol phosphate, 0.54% by weight of formalin solution and 40.66% by weight of water at room temperature. The formulation was stored for some weeks and was technologically stable. pH 7, viscosity 290 mPa.s.

EXAMPLE 5

30% by weight of sunflower lecithin are stirred into a mixture consisting of 1.0% by weight of aminoalkanol, 1.0% by weight of ethoxylated coconut oil amine, 2.0% by weight of ethoxylated oxo-alcohol, 0.5% by weight of formalin solution, 5% by weight of 1-hydroxy-2-trimethylamino-ethane hydrochloride and 60.46% by weight of water at room temperature.

The resulting formulation with a pH of 8.5 and a viscosity of about 200 mPa.s was stored for some months and remained technologically stable.

EXAMPLE 6

51.4% by weight of soya lecithin wet sludge are stirred into a mixture consisting of 1.0% by weight of aminoalkanol, 2.0% by weight of ethoxylated coconut oil amine, 1.0% by weight of alkyl polyglycol ether, 5.0% by weight of trimethylamino-alkanol hydrochloride, 0.54% by weight of formalin solution and 39.06% by weight of water at room temperature. Viscosity less than 100 mPa.s, pHl7. After some weeks, the formulation was technologically stable.

EXAMPLE 7

30% by weight of soya lecithin, corresponding to 30% of crude phosphatide, are mixed with a mixture consisting of
1.5% by weight of alkyl polyglycol ether
1.5% by weight of ethoxylated coconut oil amine
1.0% by weight of 2-amino-1-hydroxy-propane
7.0% by weight of 2-hydroxy-1-trimethylamino-propane and
59.0% by weight of water at room temperature for 20 minutes, with stirring. The resulting homogeneous liquid has a viscosity of 140 mPa.s and can be diluted with water in all proportions. It meets the requirements for the preparation of spray liquors of plant treatment agents.

EXAMPLE 8

30% by weight of rape lecithin are stirred with a mixture consisting of
1.5% by weight of alkyl polyglycol ether
1.5% by weight of ethoxylated coconut oil amine
1.0% by weight of 2-amino-1-hydroxy-propane
7.0% by weight of 1-hydroxy-2-trimethylamino-propane and
59.0% by weight of water analogously to Example 7. The resulting homogeneous product has a viscosity of 400 mPa.s.

EXAMPLE 9

20% by weight of Phospholipon ® 25 are stirred into a solution of 1.0% by weight of 1-amino-2-hydroxy-ethane and 5.0% by weight of 1-hydroxy-2-trimethylamino-ethane hydrochloride as well as 1.0% by weight of Preventol D 3 (preservative: synergistically active mixture of arylmethanol and halogenoacylaminoethanol) and 73% by weight of water. The resulting emulsion with a pH of about 8 and a viscosity of less than 100 mPa.s was stored for several months and was technologically stable.

EXAMPLE 10

20% by weight of Phospholipon ® 38 are stirred into a mixture consisting of 1.0% by weight of 1-amino-2-hydroxy-ethane, 0.54% by weight of formalin, 5.0% by weight of 1-hydroxy-2-trimethylamino-ethane hydrochloride and 73.46% by weight of water at room temperature.

The resulting formulation with a pH of 9 and viscosity of less than 100 mPa.s was stored for some months and was technologically stable.

EXAMPLE 11

20% by weight os Phospholipon ® 80 are stirred into a mixture consisting of 1.0% by weight of 1-amino-2-hydroxy-ethane, 0.54% by weight of formalin, 5.0% by weight of 1-hydroxy-2-trimethylamino-ethane hydrochloride and 73.46% by weight of water at room temperature.

The resulting formulation with a pH of 9 and a viscosity of less than 100 mPa.s was stored for some months and was technologically stable.

EXAMPLE 12

30% by weight of Phospholipon ® 100 are stirred into a mixture consisting of 1.0% by weight of 1-amino-2-hydroxy-ethane, 0.54% by weight of formalin, 5.0% by weight of 1-hydroxy-2-trimethylamino-ethane hydrochloride and 63.46% by weight of water at room temperature.

The resulting formulation with a pH of 9 and a viscosity of less than 100 mPa.s was stored for some months and was technologically stable.

Comparison of products prepared without the compounds of the formula I mentioned in the present invention application or with these.

EXAMPLE 13

61.1% by weight of soya lecithin wet sludge, corresponding to 30% by weight of soya lecithin, are mixed with 38.9% by weight of water at rooim temperature for 1 hour, with stirring. The resulting homogeneous viscous product has a viscosity of 8,000 mPa.s, can be diluted with water only by intensive stirring and does not meet the requirements for the preparation of spray liquors of plant treatment agents.

EXAMPLE 14

30% by weight of soya lecithin are stirred with 70% by weight of water analogously to Example 13. The resulting product has a viscosity of 3,400 mPa.s and likewise does not meet the requirements for the preparation of spray liquors of plant treatment agents.

EXAMPLE 15

20% by weight of Phospholipon ® 80 are mixed with 80% of water analogously to Example 13. The resulting product has a viscosity of about 17,000 mPa.s and can be diluted with water only with the aid of a stirrer or mixer.

EXAMPLE 16

30% by weight of Phospholipon ® 100 are mixed with 70% by weight of water analogously to Example 13. The resulting product has a viscosity of about 7,000 mPa.s and can be diluted with water only with the aid of a stirrer or mixer.

Chlorthelonil
(Re 3)
Leaf fertilizers, inter alia, with the following composition were tested:

|  | Type A | Type B |
|---|---|---|
| N | 20 | 8 |
| $P_2O_5$ | 10 | 8 |
| $K_2O$ | 15 | 6 |
| MgO | 4 | 0.01 |
| Fe | 0.4 | 0.01 |
| Zn | 0.1 | 0.01 |
| Mn | 0.15 | 0.01 |
| Other trace elements | 0.1 | 0.025 |

Results

If Examples 1–12, prepared with the compositions according to the invention, are compared with Examples 13–16, prepared without the addition, according to the invention, of compounds of the formula I, it can be clearly seen with the aid of the preceding table that only the products prepared according to the invention meet the requirement of a dilution with water which can be prepared in all proportions by simple mixing without mechanical assistance.

It can furthermore be seen that the requirement of compatibility with herbicide/fungicide spray liquors or leaf fertilizer application solutions is met only by the formulations prepared according to the invention.

EXAMPLE 17

| Composition according to | Phospholipid concentration | Viscosity in mPa.s | Appearance of the 10% strength formulation dispersion without mechanical assistance | Compatibility of the formulation dispersion with Herbicide spray Liquors[1] | Fungicide spray Liquors[2] | Leaf fertilizer application solutions[3] |
|---|---|---|---|---|---|---|
| Example 11 |  | 100 | homogeneous | + | + | + |
| Example 15 | 20% of Phospholipon$^R$ 80 | 17,000 | inhomogeneous, lumpy | − | − | − |
| Example 12 |  | 100 | homogeneous | + | + | + |
| Example 16 | 30% of Phospholipon$^R$ 100 | 7,000 | inhomogeneous, lumpy | − | − | − |
| Example 6 |  | 100 | homogeneous | + | + | + |
| Example 13 | 30% of soya Lecithin wet sludge | 8,000 | inhomogeneous, lumpy | − | − | − |
| Example 2 |  | 100 | homogeneous | + | + | + |
| Example 14 | 30% of soya Lecithin | 3,400 | inhomogeneous, lumpy | − | − | − |
| Example 9 | 20% of Phospholipon$^R$ 25 | 100 | homogeneous | + | + | + |
| Example 10 | 20% of Phospholipon$^R$ 38 | 100 | homogeneous | + | + | + |

+ = the formulation dispersion in water is compatible with the spray liquor or application solution
− = the formulation dispersion in water is incompatible with the spray liquor or application solution (Re 1)
The following active compounds, inter alia, were tested in the form of commercial products in the herbicide spray liquors:
  Atrazin
  Isoproturon
(Re 2)
The following active compounds, inter alia, were tested in the form of commercial products in the fungicide spray liquors:
  Folpet
  Procymidon A spray liquor corresponding to 3.0 liters of commercial product (active ingredient=Isoproturon) per hectare is prepared by dilution with water and its surface tension is measured as 51.8 mN/m by means of a Tensiomat ®. The surface tension is reduced to 39 mN/m by addition of the product of Example 11 in an amount of 4 k/ha and a substantially better wetting of the leaf surface after application of the spray liquor is thereby achieved.

Since only low mechanical forces are available for preparation of the spray liquors of plant treatment agents, the products to be processed to give the spray liquor must be dispersed or emulsified virtually spontaneously in water, whether solid or liquid. Mixing the products with water is merely brought about by pumping in circulation.

EXAMPLE 18

The results of biological tests under greenhouse conditions are shown in the following table. In these tests, the active compounds formulated as commercial products were applied in the form of spray liquors (A) or in the form of tank mixes (B).

Tank mixes (B) are to be understood as spray liquors which are prepared by dilution of a commerical product with water and addition of a product, in the present case prepared according to the invention, based on lecithin wet sludge.

The results of biological herbicide tests are shown as percentage damage to the plants (weeds) treated with spray liquors or tank mixes.

0% means no damage, that is to say ineffective, and 100% means total damage, that is to say maximum activity.

In each case the experiments a and b with the same number are to be compared.

The suitability of the addition of the examples prepared according to the invention is shown in the higher damage percentages.

In the case of the present biological test with growth regulators, the height of the stems is measured in cm. Shortening of the stem is a desirable effect.

In the case of the biological test described with fungicides, the degree of infection (DI) and degree of action (DA) in combating Botrytis in wine-growing are determined. The lower the degree of infection and the higher the degree of action, the more effective is the fungicide treatment.

| Biological tests - Example 12 | | | | | | | | | |
|---|---|---|---|---|---|---|---|---|---|
| Commercial product (CP) | | Types of spray Liquor | | Damage to the weeds in % | | | | | |
| No. | Active compound | CP per hectare | A | B | Sinapis alba | Poa annua | Panicum milaceum | Solanum Lycopersicum | Alopecurus myosaroide |
| 0 | 1 | 2 | 3 | 4 | 5 | 6 | 7 | 8 | 9 |
| 1a | Isoproturon | 0.700 kg | CP | | 35 | | 30 | 20 | 30 |
| 1b | | 0.700 kg | | CP + Example 3 | 67 | | 75 | 57 | 58 |
| 2a | Isoproturon | 0.700 kg | CP | | 40 | | 27 | 30 | 45 |
| 2b | | 0.700 kg | | CP + Example 5 | 81 | | 50 | 37 | 60 |
| 3a | Isoproturon | 1.000 kg | CP | | 40 | | 33 | 30 | 50 |
| 3b | | 1.000 kg | | CP + Example 6 | 70 | | 73 | 85 | 60 |
| 4a | Metamitron | 2.000 kg | CP | | 45 | | 20 | 35 | 31 |
| 4b | | 2.000 kg | | CP + Example 3 | 55 | | 30 | 45 | 40 |
| 5a | Metamitron | 2.000 kg | CP | | 52 | | 0 | 40 | |
| 5b | | 2.000 kg | | CP + Example 1 | 75 | | 10 | 60 | |
| 6a | Atrazine | 1.875 kg | CP | | 50 | 20 | 10 | 45 | |
| 6b | | 1.875 kg | | CP + Example 3 | 80 | 35 | 15 | 88 | |
| 7a | Atrazine | 2.000 kg | CP | | 50 | | 8 | | |
| 7b | | 2.000 kg | | CP + Example 4 | 75 | | 10 | | |
| 8a | Atrazine | 1.875 kg | CP | | 50 | 20 | 10 | 40 | |
| 8b | | 1.875 kg | | CP + Example 2 | 93 | 36 | 13 | 85 | |
| 9a | Diuron | 2.000 kg | CP | | 59 | | | 14 | 15 |
| 9b | | 2.000 kg | | CP + Example 1 | 84 | | | 58 | 43 |
| 10a | Linuron | 1.000 kg | CP | | 71 | | 60 | 29 | |
| 10b | | 1.000 kg | | CP + Example 7 | 83 | | 84 | 36 | |

| Experiments with growth regulators Test plant: Winter wheat | | | |
|---|---|---|---|
| No. | Treatment | Amount applied in liters/ha | Height of the stems in cm |
| 1. | Control (untreated) | — | 44 |
| 2. | Etophon/Mepiquat chloride commercial product | 2.5 | 38 |
| 3. | No.2 + Example 20 | 2.5 + 2 | 25 |

| Experiments on combating Botrytis Test plant: Vine, Muller-Thurgau variety | | | |
|---|---|---|---|
| | | Concentration in the spray | DI | DA |

| No. | Treatment | Liquor | % | % |
|---|---|---|---|---|
| 1. | Control | Example 10, 0.4% | 35 | 0 |
| 2. | Folpet commercial product | 0.15 | 16 | 51 |
| 3. | Folpet commercial product + Example 10 | 0.15 0.4 | 8 | 74 |

DI = Degree of infection
DA = Degree of action

EXAMPLE 19

30% by weight of soya lecithin are stirred into a mixture of 1.0% by weight of 1-amino-2-hydroxy-alkane, 4.5% by weight of ethoxylated coconut alkylamine, 4.5% by weight of alkyl polyglycol ether, 7% by weight of 70% strength 1-hydroxy-2-trimethylammonium chloride-alkane and 53% by weight of water at room temperature. The resulting formulation has a viscosity of 200 mPa.s and was technologically stable for several months.

EXAMPLE 20

30% by weight of soya lecithin are stirred into a mixture of 1.0% by weight of 1-amino-2-hydroxy-alkane, 7.5% by weight of ethoxylated coconut alkylamine, 7.5% by weight of arylalkylpolyglycol ether, 7% by weight of 70% strength 1-hydroxy-2-trimethylammonium chloride-alkane and 47% by weight of water at room temperature. The resulting formulation has a viscosity of 180 mPa.s and was technologically stable for several months.

EXAMPLE 21

30% by weight of soya lecithin are stirred into a mixture of 1.0% by weight of 1-amino-2-hydroxy-alkane, 7% by weight of 70% strength 1-hydroxy-2-trimethylammonium chloride-alkane, 15% by weight of ethoxylated fatty alcohol and 47% by weight of water at room temperature. The resulting formulation has a viscosity of 120 mPa.s and was technologiclly stable for several months.

EXAMPLE 22

10 kg of lecithin-containing product prepared analogously to Example 2 (preservative K sorbate+sodium benzoate) are kneaded with 100 kg of wheat flour grade 550, 4 kg of yeast, 2 kg of salt, 1 kg of peanut fat, 1 kg of sugar, 3 g of ascorbic acid, 400 g of calcium acetate and 50 kg of water. Temperature of the kneaded mass 30° C., kneading time 2 minutes. The resulting mass is left to rest for 15 minutes. After an intermediate fermentation time of 10 minutes and a final fermentation time of 90 minutes, a high-quality baking agent is obtained.

EXAMPLE 23

2 kg of lecithin-containing product prepared according to Example 2 are mixed with 13 kg of zinc oxide, 11 kg of titanium dioxide, 5.5 kg of chalk, 6 kg of kaolin, 200 g of sodium potassium hexametaphosphate, 4.3 kg of stabilizer, 19 kg of water and 39 kg of polyvinyl ester to give a sterile dispersion.

EXAMPLE 24

Lecithin-containing product, prepared according to Example 2 and preserved with K sorbate and sodium benzoate, is sprayed onto dried milk in a ratio of 0.8–2 to 1,000. The resulting whole milk powder has good instant properties.

EXAMPLE 25

5 kg of crude coffee are warmed to 220° C. in a roasting unit. After this temperature has been reached, a lecithin-containing product, prepared according to Example 11 (preservative sodium benzoate+potassium sorbate) is sprayed on in an amount such that the dried roasted coffee beans are coated with about 10 g of lecithin per kg of roasted coffee beans.

The coffee beans provided with aroma protection in this way can be ground in the customary manner and processed to coffee drinks.

EXAMPLE 26

10.6 kg of wheatgerm oil, 1.7 kg of beeswax, 1.7 kg of oleum cacao DAB 8, 1.2 kg of cetylstearyl alcohol DAB 8, 2.1 kg of wool wax DAB 8, 0.8 kg of polyoxyethylene sorbitan monooleate and 0.08 kg of benzoic acid are melted at 70° C. and mixed. 16.6 kg of lecithin-containing product prepared according to Example 12 are slowly stirred in and the mixture is subsequently topped up with 22 kg of water. The resulting mass is cooled, with stirring, and is homogenized after reaching room temperature. The product prepared according to Example 26 can be used as a cosmetic moisturizing cream.

What is claimed is:

1. An aqueous phospholipid solution comprising as a solubilizing agent at least one of (1) one or more compounds of the formula I $$RO-A-NR_1R_2$$

in which R denotes hydrogen or an acyl radical of a carboxylic acid having 1–22 carbon atoms, A denotes a straight-chain or branched alkylene group having 1–10 carbon atoms and $R_1$ and $R_2$, which are identical or different denote hydrogen or an alkyl group having 1–8 carbon atoms, or (2) one or more salts of an inorganic or an organic acid and ($RO-A-N^+R_1R_2R_3$) wherein R, A, $R_1$ and $R_2$ are as defined above and $R_3$ denotes a hydrogen or an alkyl group having 1–8 carbon atoms.

2. An aqueous phospholipid solution as claimed in claim 1 wherein R denotes hydrogen, A denotes a straight-chain alkylene group having 2–4 carbon atoms and $R_1$, $R_2$ and $R_3$ are identical or different and denote hydrogen or methyl.

3. An aqueous phospholipid solution as claimed in claim 1, in which at least one of 1-amino-2-hydroxy-alkanes and 1-hydroxy-2-trimethylamino-alkanes are employed as the solubilizing agent.

4. An aqueous phospholipid solution as claimed in claim 1, in which a mixture of 1-amino-2-hydroxy-alkane and 1-hydroxy-2-trimethylamino-alkane is employed as the solubilizing agent.

5. An aqueous phospholipid solution as claimed in claim 4, in which 1-amino-2-hydroxy-alkane, 1-amino-2-hydroxy-ethane, 1-amino-2-hydroxy-propane, 1-amino-2-hydroxy-butane, 1-amino-2-hydroxy-pentane or 1-amino-2-hydroxy-hexane is employed as the solubilizing agent.

6. An aqueous phospholipid solution as claimed in claim 4, in which 1-hydroxy-2-trimethylamino-alkane, 1-hydroxy-2-trimethylamino-ethane, 1-hydroxy-2-trimethylamino-propane, 1-hydroxy-2-trimethylamino-butane, 1-hydroxy-2-trimethylamino-pentane or 1-hydroxy-2-trimethylamino-hexane is employed as the solubilizing agent.

7. An aqueous phospholipid solution as claimed in claim 1, in which a mixture of 1-amino-2-hydroxy-ethane and 1-hydroxy-2-trimethylamino-ethane-hydrochloride is used as the solubilizing agent.

8. An aqueous phospholipid solution as claimed in claim 7, in which the solubilizing agent mixture of 1-amino-2-hydroxy-alkane and 1-hydroxy-2-trimethylamino-ethane-hydrochloride in a weight ratio of 1:5 is employed.

9. An aqueous phospholipid solution as claimed in claim 1, in which 3–10% by weight of the solubilizing agent or solubilizing agent mixture is employed.

10. An aqueous phospholipid solution as claimed in claim 1, in which 5–7% by weight of the solubilizing agent or solubilizing agent mixture is employed.

11. An aqueous phospholipid solution as claimed in claim 1, in which 6% by weight of the solubilizing agent or solubilizing agent mixture is employed.

12. An aqueous phospholipid solution as claimed in claim 1, in which the phospholipid content in the solution is 5–80% by weight.

* * * * *